United States Patent [19]

Weber et al.

[11] 4,263,431
[45] Apr. 21, 1981

[54] CATIONIC FLUORESCENT WHITENING AGENTS

[75] Inventors: Kurt Weber; Christian Lüthi, both of Basel; Hans R. Meyer, Binningen, all of Switzerland

[73] Assignee: Ciba-Geigy Corporation, Ardsley, N.Y.

[21] Appl. No.: 39,722

[22] Filed: May 17, 1979

[30] Foreign Application Priority Data

May 29, 1978 [CH] Switzerland ............... 5844/78

[51] Int. Cl.³ ............ C07D 207/12; C07D 231/06; C07D 401/02
[52] U.S. Cl. ............... 542/459; 260/326 C; 260/924; 544/110; 544/371; 544/372; 544/383; 546/200; 546/211; 548/379; 542/464; 252/301.21; 252/301.22; 252/301.25; 252/301.26; 252/301.27
[58] Field of Search ............... 260/924, 326 R; 548/379; 544/110, 371, 372, 383; 546/200, 211; 542/459, 464

[56] References Cited

U.S. PATENT DOCUMENTS

| | | | |
|---|---|---|---|
| 2,824,113 | 2/1958 | Zech | 260/924 |
| 3,507,937 | 4/1970 | Zimmerer | 260/924 |
| 3,574,195 | 4/1971 | Hajer | 548/379 |
| 3,630,895 | 12/1971 | Krause | 548/379 |
| 3,690,947 | 9/1972 | Rosch | 548/379 |
| 3,714,256 | 1/1973 | Samour et al. | 260/924 |
| 3,849,406 | 11/1974 | Aebil et al. | 548/379 |
| 3,984,399 | 10/1976 | Weber et al. | 542/464 |
| 4,045,169 | 8/1977 | Mengler | 548/379 |
| 4,085,101 | 4/1978 | Mercer et al. | 548/379 |
| 4,147,743 | 4/1979 | Bathelt | 260/924 |

*Primary Examiner*—Arthur P. Demers
*Attorney, Agent, or Firm*—Edward McC. Roberts; John P. Spitals

[57] ABSTRACT

The invention relates to cationic fluorescent whitening agents of the formula

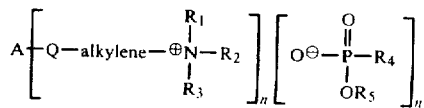

wherein A is the radical of a fluorescent whitening agent, Q is the direct bond or a bridge member, $R_1$ to $R_5$ are specific substituents and n is 1 or 2. A process for the manufacture of these compounds and a method of whitening organic material which comprises their use are also disclosed.

9 Claims, No Drawings

CATIONIC FLUORESCENT WHITENING AGENTS

The present invention relates to novel cationic fluorescent whitening agents, a process for their manufacture and a method of whitening organic material which comprises the use thereof.

Cationic fluorescent whitening agents are known from the literature, for example from German Offenlegungsschriften Nos. 1,670,980, 1,155,418, 1,469,222, 2,011,552, 2,145,019 and 2,248,772, German Auslegeschriften 1,904,424, 1,793,482 and 1,794,386, and from French Pat. No. 2,303,012. These cationic fluorescent whitening agents have only limited solubility at room temperature in water and polar organic solvents.

The invention provides cationic fluorescent whitening agents of the formula

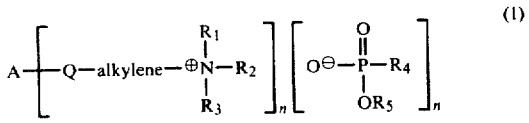

wherein
A represents the radical of a fluorescent whitening agent,
Q represents the direct bond or a bridge member,
$R_1$ represent unsubstituted or substituted alkyl, alkenyl or aralkyl or together with $R_2$ or Q forms a heterocyclic ring,
$R_2$ represents unsubstituted or substituted alkyl, alkenyl or aralkyl or together with $R_1$ forms a heterocyclic ring,
$R_3$ represents alkyl of 1 to 4 carbon atoms,
$R_4$ represents hydrogen or unsubstituted or substituted alkyl,
$R_5$ represents alkyl of 1 to 4 carbon atoms, and
n is 1 or 2.

Compared with the compounds of the prior art cited above, the cationic fluorescent whitening agents of this invention are distinguished by improved solubility in water and polar organic solvents at room temperature. This improved solubility makes it possible to prepare fluorescent whitener solutions with concentrations of up to 60% by weight, preferably of 10 to 50% by weight, of fluorescent whitening agent.

Suitable radicals A are, for example, radicals of fluorescent whitening agents of the series of the 1,3-diarylpyrazolines, preferably 1,3-diphenylpyrazolines, 4,4'-distyrylbiphenyls, coumarins which are substituted in the 3- and 7-position, naphthalimides, 2-stilben-4-yl-naphthotriazoles, ethylene-bis-benzoxazoles, 4,4'-bis-(triazinylamino)-stilbenes, 4,4'-bis-(v-triazol-2-yl)-stilbenes and 4,4'-bis-(pyrazol-2-yl)-stilbenes, and of the phenylfurane- and benzofuranebenzimidazoles.

Possible bridge members Q are non-chromophoric groups, such as —$SO_2$—alkyleneoxy containing 2 to 8, preferably 2 to 4, carbon atoms in the alkyl moiety, —COO—, —$SO_2$—, —$SO_2$—alkylene—CON(R)— and —$SO_2$N(R)—, wherein "alkylene" contains 2 to 8, preferably 2 to 4, carbon atoms, and R represents hydrogen or alkyl of 1 to 6, preferably 1 to 4, carbon atoms, which can be substituted e.g. by cyano, carbamoyl, carboxyl, carbalkoxy, hydroxyl, halogen, alkoxy of 1 to 4 carbon atoms.

If A is the radical of a 1,3-diarylpyrazoline system, then the following radicals are particularly preferred as bridge members Q: —$SO_2$—alkyleneoxy containing 2 to 8, preferably 2 to 4, carbon atoms in the alkylene moiety, —$SO_2$—alkylene—COO— containing 2 to 8, preferably 2 to 4, carbon atoms in the alkylene moiety, —COO—, —$SO_2$— and —$SO_2$—alkylene—CON(R)—, wherein "alkylene" and R are as defined above. If A is the radical of a 4,4'-distyrylbiphenyl, then the bridge member Q is most preferably the radical —$SO_2N(R)$—, wherein R is as defined above.

Suitable alkyl radicals $R_1$ and $R_2$ are those containing 1 to 6, preferably 1 to 4, carbon atoms. They can be substituted e.g. by halogen, cyano, hydroxyl, alkoxycarbonyl of 1 to 4 carbon atoms or alkylcarbonyloxy of 1 to 4 carbon atoms.

Alkenyl radicals $R_1$ and $R_2$ contain preferably 2 to 4 carbon atoms. Suitable aralkyl radicals $R_1$ and $R_2$ are preferably the benzyl and phenethyl radical, which can be substituted in the benzene rings by halogen, alkyl of 1 to 4 carbon atoms or alkoxy of 1 to 4 carbon atoms.

The substituents $R_1$ and $R_2$ together can form a 5- or 6-membered heterocyclic ring, for example a piperidine, pyrrolidine or morpholine ring, which can be substituted by alkyl groups of 1 to 4 carbon atoms.

Suitable alkyl radicals $R_4$ contain preferably 1 to 4 carbon atoms and can be substituted by hydroxyl, cyano, alkylcarbonyloxy or alkoxycarbonyl each containing 1 to 4 carbon atoms in the alkyl moiety.

By "alkylene" is meant a bivalent straight chain or branched alkylene chain containing 2 to 20, preferably 2 to 12 and most particularly 2 to 6, carbon atoms.

Within the scope of the present invention, particularly interesting cationic fluorescent whitening agents are those of the formula

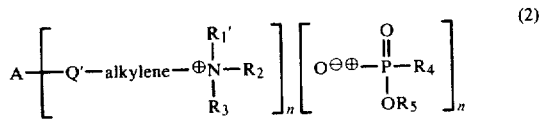

wherein A, $R_2$ to $R_5$ and n have the given meanings, Q' represents —$SO_2$—alkyleneoxy containing 2 to 4 carbon atoms, —$SO_2$—alkylene—COO— containing 2 to 4 carbon atoms, —$SO_2$—, —COO—, —$SO_2$—alkylene—CON($R_6$)— or —$SO_2N(R_6)$—, wherein $R_6$ represents hydrogen, substituted or unsubstituted alkyl of 1 to 5 carbon atoms or together with $R_1'$ represents a piperazine radical, and $R_1'$ represents unsubstituted or substituted alkyl, alkenyl or aralkyl, together with $R_6$ represents a piperazine radical or together with $R_2$ forms a heterocyclic ring.

Preferred cationic fluorescent whitening agents are those of the formula

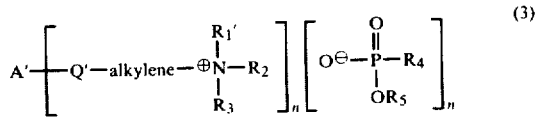

wherein Q', $R_1'$, $R_2$ to $R_5$ and n have the given meanings and A' represents a radical of the formula

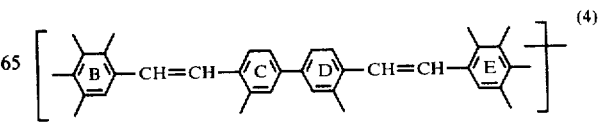

or of the formula

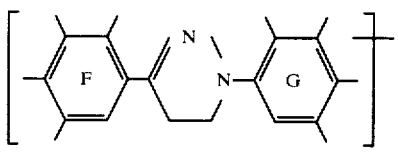

the benzene rings of which formulae can also be substituted by non-chromophoric substituents at the indicated positions.

Examples of non-chromophoric substituents are: halogen atoms; alkyl groups, which can also be substituted e.g. by halogen, cyano, alkoxy, phenoxy or aryl, preferably phenyl; cycloalkyl groups; alkenyl groups; alkoxy groups, which can also be substituted e.g. by halogen, alkoxy, aryl, preferably phenyl or phenoxy; alkenyloxy groups; sulfonyl groups, for example alkyl- or phenylsulfonyl groups; aryl or aryloxy groups, preferably phenyl or phenoxy groups, which can be substituted by one or more of the above mentioned radicals; cyano groups; carbalkoxy groups; carbamoyl groups; sulfamoyl groups.

Preferred cationic fluorescent whitening agents have the formula

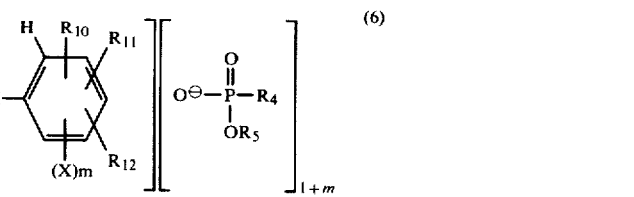

wherein $R_4$ and $R_5$ have the above meanings, m is 0 or 1, $R_7$ represents hydrogen, alkyl of 1 to 4 carbon atoms, alkoxy of 1 to 4 carbon atoms or halogen, $R_8$ represents hydrogen, alkyl of 1 to 4 carbon atoms, alkoxy of 1 to 4 carbon atoms or halogen, $R_9$ represents hydrogen or alkyl of 1 to 4 carbon atoms, $R_{10}$, $R_{11}$ and $R_{12}$, if m is 1, have the meanings of $R_7$, $R_8$ and $R_9$ or, if m is 0, each of $R_{10}$, $R_{11}$ and $R_{12}$ independently represents hydrogen, alkyl of 1 to 4 carbon atoms, alkoxy of 1 to 4 carbon atoms or halogen, and X represents the radical

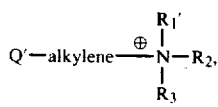

wherein Q', $R_1'$, $R_2$ and $R_3$ have the indicated meanings.

Particularly preferred cationic fluorescent whitening agents are those of the formula wherein Q" represents —COO—, —CON($R_6$)— or —SO$_2$N($R_6$)—, $R_1'$ represents unsubstituted or substituted alkyl, alkenyl or aralkyl, together with $R_6$ represents a piperazine radical or together with $R_2'$ represents a pyrrolidine, piperidine or morpholine radical, $R_2'$ represents unsubstituted or substituted alkyl, alkenyl or aralkyl or together with $R_1'$ represents a pyrrolidine, piperidine or morpholine radical, $R_3$ represents alkyl of 1 to 4 carbon atoms, $R_4$ represents hydrogen or unsubstituted or substituted alkyl, $R_5$ represents alkyl of 1 to 4 carbon atoms, $R_6$ represents hydrogen, unsubstituted or substituted alkyl of 1 to 5 carbon atoms or together with $R_1'$ represents a piperazine radical, $R_7'$ represents hydrogen, chlorine, alkyl of 1 to 4 carbon atoms, or alkoxy of 1 to 4 carbon atoms, $R_8'$ represents hydrogen, chlorine, alkyl of 1 to 4 carbon atoms or alkoxy of 1 to 4 carbon atoms, $R_9$ represents hydrogen or alkyl of 1 to 4 carbon atoms, and Z represents alkylene of 2 to 5 carbon atoms, and those of the formula

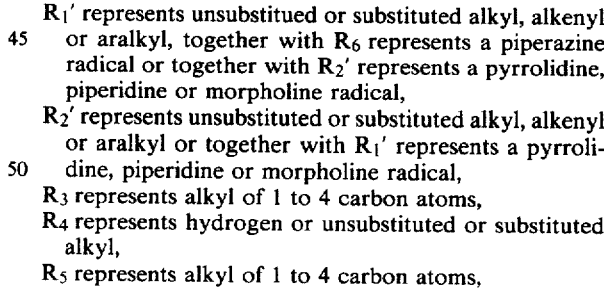

wherein $R_1'$ represents unsubstitued or substituted alkyl, alkenyl or aralkyl, together with $R_6$ represents a piperazine radical or together with $R_2'$ represents a pyrrolidine, piperidine or morpholine radical, $R_2'$ represents unsubstituted or substituted alkyl, alkenyl or aralkyl or together with $R_1'$ represents a pyrrolidine, piperidine or morpholine radical, $R_3$ represents alkyl of 1 to 4 carbon atoms, $R_4$ represents hydrogen or unsubstituted or substituted alkyl, $R_5$ represents alkyl of 1 to 4 carbon atoms,

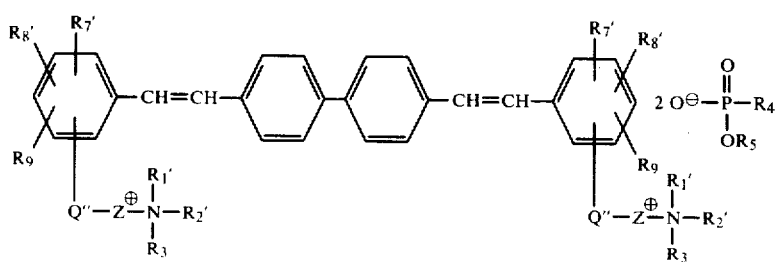

$R_{13}$, $R_{14}$ and $R_{15}$, each independently of the other, represent hydrogen, chlorine, alkyl of 1 to 4 carbon atoms or alkoxy of 1 to 4 carbon atoms, Y represents alkylene of 2 or 3 carbon atoms, —N(R$_6$)— alkylene containing 2 to 5 carbon atoms in the alkylene moiety, alkyleneoxyalkylene containing altogether 4 to 8 carbon atoms, alkylene—COO— alkylene or alkylene—CON(R$_6$)—alkylene, each containing altogether 4 to 8 carbon atoms in the alkylene moiety, and $R_6$ represents hydrogen, unsubstituted or substituted alkyl of 1 to 5 carbon atoms or together with $R_1'$ represents a piperazine radical.

The most preferred cationic fluorescent whitening agents are those of the formula

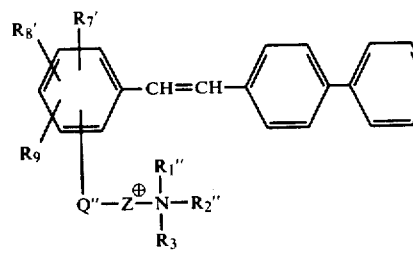 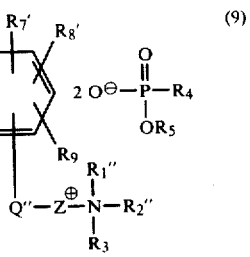

(9)

wherein
$R_3$ to $R_5$, $R_7'$, $R_8'$, $R_9$ and Z have the given meanings,
Q'' represents —COO—, —CON(R$_6$)— or —SO$_2$N(R$_6$)—, wherein $R_6$ represents hydrogen, unsubstituted or substituted alkyl of 1 to 5 carbon atoms or together with $R_1''$ represents a piperazine radical,
$R_1''$ represents unsubstituted alkyl of 1 to 4 carbon atoms or together with $R_6$ represents a piperazine radical, and
$R_2''$ represents unsubstituted alkyl of 1 to 4 carbon atoms,
and those of the formula

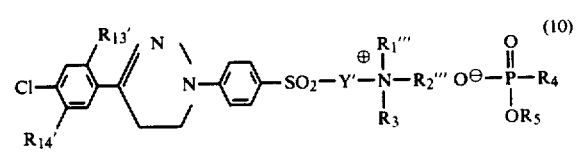

(10)

wherein
$R_3$, $R_4$ and $R_5$ have the given meanings,
$R_1'''$ represents unsubstituted or substituted alkyl of 1 to 4 carbon atoms, together with $R_6$ represents a piperazine radical or together with $R_2'''$ represents a pyrrolidine, piperidine or morpholine radical,
$R_2'''$ represents unsubstituted or substituted alkyl of 1 to 4 carbon atoms or together with $R_1'''$ represents a pyrrolidine, piperidine or morpholine radical,
$R_{13}'$ represents hydrogen or alkyl of 1 to 4 carbon atoms,
$R_{14}'$ represents hydrogen or chlorine,
Y' represents alkylene of 2 or 3 carbon atoms, —N(R$_6$)— alkylene containing 2 to 5 carbon atoms in the alkylene moiety, alkyleneoxyalkylene or alkylene—COO— alkylene, each containing altogether 4 to 6 carbon atoms in the alkylene moiety, or alkylene—CON(R$_6$)— alkylene containing altogether 4 to 8 carbon atoms in each alkylene moiety, and
$R_6$ represents hydrogen, unsubstituted or substituted alkyl of 1 to 5 carbon atoms or together with $R_1'''$ represents a piperazine radical,
and especially that of the formula

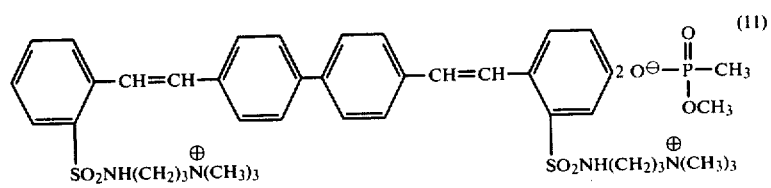

(11)

and that of the formula

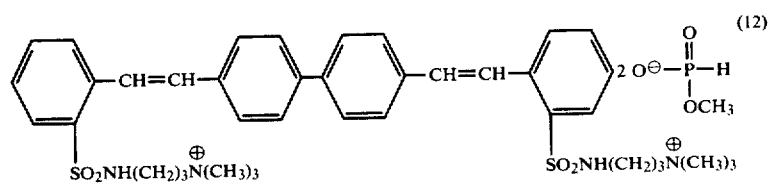

(12)

The fluorescent whitening agents of the formula (1) are obtained by reacting fluorescent whitening agents of the formula

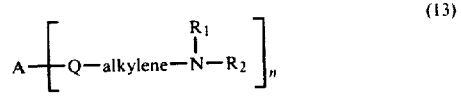

(13)

with phosphites or phosphonates of the formula

(14)

in which formulae A, Q, $R_1$ to $R_5$ and n have the given meanings.

Preferred phosphites and phosphonates are e.g.: dimethyl phosphite, diethyl phosphite, dimethyl methanephosphonate, diethyl methanephosphonate, methylethyl methanephosphonate, methylpropyl methanephosphonate, methylbutyl methanephosphonate, methylhexyl methanephosphonate, methyloctyl methanephosphonate, methyldecyl methanephosphonate, methyldodecyl methanephosphonate, dimethyl-$\beta$-hydroxy-ethanephosphonate, dimethyl-$\beta$-acetoxyethanephosphonate, dimethyl-$\beta$-methoxycarbonyle-thanephosphonate, dimethyl-$\beta$-cyanoethanephosphonate.

The reaction is carried out in water and/or organic solvents, such as methanol, ethanol, propanol, isopropanol, butanol, glycol, glycol methyl ether, glycol dimethyl ether, glycol butyl ether, diglycol methyl ether, methyl ethyl ketone, dimethyl formamide, sulfolane, oxypropionitrile, toluene, xylene, benzyl alcohol, phenoxyethanol, benzyloxypropionitrile, preferably in the temperature range from 60° to 190° C. When using liquid compounds of the formula (14), the reaction can also be carried out in the absence of an additional solvent.

A particular advantage of the cationic fluorescent whitening agents of the present invention is that they are very readily water-soluble, so that ready for use, concentrated, stable solutions are obtained without isolating the fluorescent whitening agent. These solutions are also storable at low temperature.

The novel compounds defined above exhibit a more or less pronounced fluorescence in the dissolved or finely divided state. They can be used for whitening a wide variety of synthetic, regenerated made-made or natural organic materials or substances which contain such organic materials. The organic materials to be whitened can be in the most widely different states of processing (raw materials, semi-finished goods or finished goods).

The compounds of the present invention are of importance, inter alia, for the treatment of textile organic materials, especially woven textiles.

Depending on the type of fluorescent whitening agent used, it can be advantageous to carry out the treatment in a neutral, alkaline or acid bath. The treatment is usually carried out at temperatures of 20° to 140° C., for example at the boiling point of the bath or near it (about 90° C.). Solutions or emulsions in organic solvents can also be used for the treatment of textile substrates according to the invention, as is practised in the dyeing industry in solvent dyeing (pad-thermofixation application, or exhaustion dyeing processes in dyeing machines).

The fluorescent whitening agents of the present invention can, for example, also be employed in the following formulations:

(a) in mixtures with dyes (shading) or pigments (coloured pigments or especially, for example, white pigments), or as an additive in dyebaths, printing pastes, discharge pastes or reserve pastes, or for the aftertreatment of dyeings, prints or discharge prints;

(b) in mixtures with carriers, wetting agents plasticisers, swelling agents, antioxidants, ultraviolet absorbers, heat stabilisers and chemical bleaching agents (chlorite bleach or bleaching bath additives);

(c) in admixture with crosslinking agents or finishing agents (for example starch or synthetic finishes), and in combination with a wide variety of textile finishing processes, especially synthetic resin finishes (for example creaseproof finishes such as wash-and-wear, permanent-press or non-iron), as well as flameproof finishes, fabric softening finishes, antisoiling finishes or antistatic finishes, or antimicrobial finishes;

(d) incorporation of the fluorescent whitening agents into polymer carriers (polymerisation, polycondensation or polyaddition products, in dissolved or dispersed form, for use e.g. in coating agents, impregnating agents or binders (solutions, dispersions and emulsions) for textiles, non-wovens, papers and leather;

(e) as additives in master batches;

(f) as additives in a wide variety of industrial products in order to render these more marketable (for example improving the appearance of soaps, detergents, pigments);

(g) in combination with other optically brightening substances;

(h) in spinning bath preparations, that is to say as additives in spinning baths which are used for improving the slip for the further processing of synthetic fibres, or from a special bath before the streching of the fibre;

(i) as scintillators for various purposes of a photographic nature, for example for electrophotographic reproduction or supersensitising;

(j) depending on the substitution as laser dyes.

If the whitening method is combined with textile treatment or finishing methods, the combined treatment can in many cases advantageously be carried out with the aid of appropriate stable preparations which contain the fluorescent whitening agents in a concentration such that the desired white effect is achieved.

In certain cases, the fluorescent whitening agents are made fully effective by an aftertreatment. This can be, for example, a chemical treatment (for example acid treatment), a heat treatment or a combined chemical/heat treatment.

The amount of fluorescent whitening agents of the present invention to be used, based on the weight of the material to be whitened, can vary within wide limits. A marked and lasting effect can be obtained even with very insignificant amounts, in certain cases e.g. 0.0001 percent by weight. But it is also possible to use amounts of up to about 0.8 percent by weight and, on occasion, up to about 2 percent by weight. For most practical purposes, it is preferably to use amounts between 0.005 and 0.5 percent by weight.

For various reasons it is often advantageous not to use the fluorescent whitening agents by themselves, i.e. pure, but in admixture with a wide variety of assistants and extenders, for example anhydrous sodium sulfate, sodium sulfate decahydrate, sodium chloride, sodium carbonate, alkali metal phosphates, such as sodium or potassium orthophosphate, sodium or potassium pyrophosphate and sodium or potassium tripolyphosphates or alkali metal silicates.

The cationic fluorescent whitening agents of the present invention are suitable for whitening organic material, especially polyacrylonitrile, acid-modified polyesters, polyamide and cellulose.

In the following Examples, percentages are by weight. Unless othewise indicated, melting and boiling points are uncorrected.

EXAMPLE 1

6.9 g of the compound of the formula

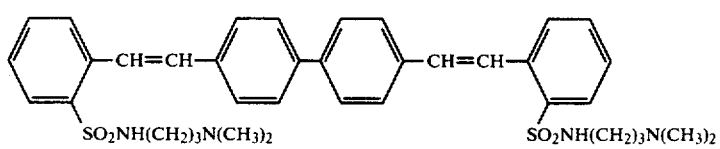

and 10.4 g of dimethyl methanephosphonate are refluxed in 22 ml of toluene for 4 hours. After cooling to room temperature, the crystallised product is filtered by suction, washed with toluene and dried in vacuo at 40°–50° C., affording 9.3 g of the compound of the formula

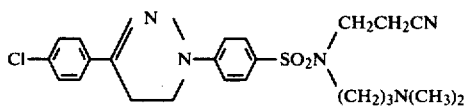

At room temperature the solubility of this product in water is about 34 g in 100 ml of water. The solubility of the methosulfate is about 2.5 g.

EXAMPLE 2

4.8 g of the compound of the formula

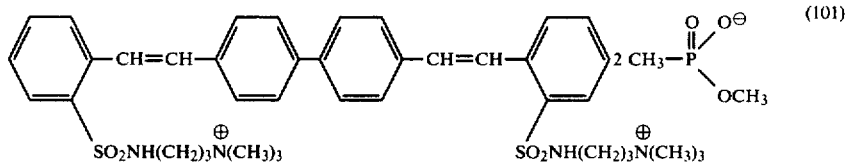

and 5.2 g of dimethyl methanephosphonate are refluxed in 22 ml of toluene for 6 hours. After cooling to room temperature, the crystallised product is filtered by suction, washed with toluene, and dried in vacuo at 40°–50° C., affording 5.5 g of the compound of the formula

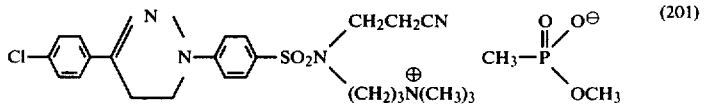

At room temperature the solubility of this product in water is about 50 g in 100 ml of water. The solubility of the corresponding methosulfate or chloride is about 1 g. The compound of the formula (200) can be obtained as follows: With stirring, 53 g of the sulfochloride of the formula

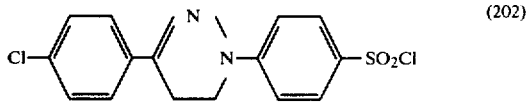

are suspended at room temperature in 360 ml of o-dichlorobenzene. Then 24.2 g of N-(3-dimethylamino-propylamino)-N-(2'-cyanoethyl)-amine of the formula

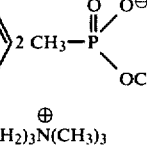

are added dropwise in the course of 30 minutes. The reaction mixture is heated to 100° C. in the course of 30 minutes and stirred for 2 hours at 100°–105° C. After cooling to 90° C., 300 ml of water are added and 20 g of 20% sodium hydroxide are added dropwise in the course of 20 minutes. The o-dichlorobenzene is then distilled off in vacuo as an azeotrope. The batch is cooled to room temperature and the crystallised product is filtered by suction, dried in vacuo at room temperature and crystallised firstly from ethanol with the aid of activated charcoal and then from toluene using fuller's earth, and finally dried in vacuo at 50°–60° C. Yield: 36.8 of the compound of the formula (200).

EXAMPLE 3

6.9 g of the compound of the formula (100) and 8.8 g of dimethyl phosphite are refluxed in 22 ml of toluene for 5 hours and worked up as described in Example 1. Yield: 9.1 g of the compound of the formula

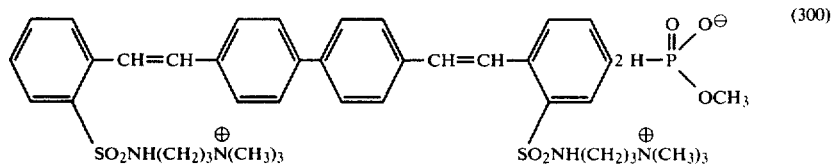

At room temperature the solubility of this product in water is about 41 g in 100 ml of water.

EXAMPLE 4

4.8 g of the compound of the formula (200) and 4.4 g of dimethyl phosphite are refluxed for 2 hours in 22 ml of toluene. Yield: 6.5 g of the very hygroscopic compound of the formula

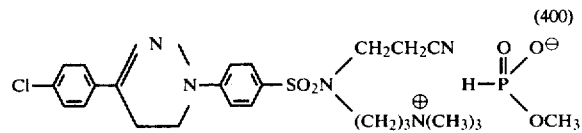
(400)

which contains about 1 mole of water of crystallisation.

The solubility of this product at room temperature in water is about 50 g in 100 ml of water.

EXAMPLE 5

With stirring, 13.7 g of the compound of the formula (100) are heated in 30.8 g of dimethyl methanephosphonate for 2 hours to 120° C. After cooling to room temperature, the mixture is diluted with water to a total weight of 52.7 g, whereupon the crystallised product dissolves. The resulting solution contains 35.5% of the compound of the formula (101).

The fluorescent whitening agents listed in Tables 1 and 2 can also be obtained in a manner similar to that described in the preceding Examples.

TABLE 1

$$\left[ B-CH=CH-\underset{}{\underset{}{\bigcirc}}-\underset{}{\underset{}{\bigcirc}}-CH=CH-B \right] 2\ A \quad (500)$$

| formula | B | A |
|---|---|---|
| 501 | —⌬—SO₂NH(CH₂)₃N⁺(CH₃)₃ | CH₃—P(=O)(O⁻)OCH₃ |
| 502 | —⌬—SO₂NH(CH₂)₂N⁺(CH₃)₃ | CH₃—P(=O)(O⁻)OCH₃ |
| 503 | —⌬—SO₂NH(CH₂)₃N⁺(C₂H₅)₂CH₃ | CH₃—P(=O)(O⁻)OCH₃ |
| 504 | —⌬(Cl)—SO₂N(CH₂CH₂CN)(CH₂)₃N⁺(CH₃)₃ | CH₃—P(=O)(O⁻)OCH₃ |
| 505 | —⌬—SO₂N(piperazinyl-N⁺(CH₃)₂) | CH₃—P(=O)(O⁻)OCH₃ |
| 506 | —⌬(Cl)—SO₂NH(CH₂)₃N⁺(CH₃)₃ | CH₃—P(=O)(O⁻)OCH₃ |
| 507 | —⌬—SO₂NH(CH₂)₃N⁺(CH₃)₃ | H—P(=O)(O⁻)OCH₃ |
| 508 | —⌬(Cl)—SO₂NH(CH₂)₃N⁺(CH₃)₃ | H—P(=O)(O⁻)OCH₃ |
| 509 | —⌬(Cl)—SO₂NH—CH₂—C(CH₃)₂—CH₂N⁺(CH₃)₃ | H—P(=O)(O⁻)OCH₃ |

TABLE 1-continued
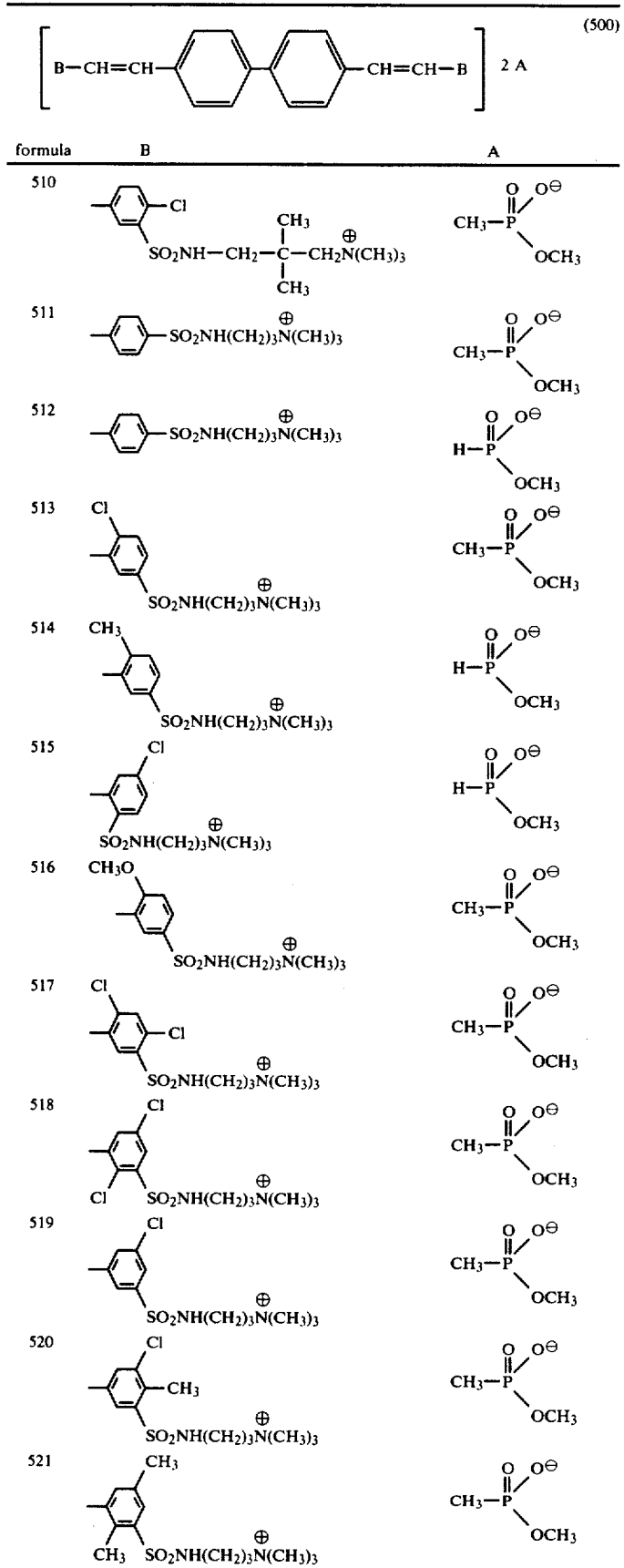

TABLE 1-continued $$\left[ B-CH=CH-\phantom{x}\underset{}{\bigcirc}-\underset{}{\bigcirc}-CH=CH-B \right] 2\ A \quad (500)$$

| formula | B | A |
|---|---|---|
| 522 | 3,5-dimethylphenyl-SO₂NH(CH₂)₃N⁺(CH₃)₃ | H—P(=O)(O⁻)(OCH₃) |
| 523 | 2,3,5-trimethyl-4-[SO₂NH(CH₂)₃N⁺(CH₃)₃]phenyl | H—P(=O)(O⁻)(OCH₃) |
| 524 | 2,3,5-trimethyl-4-[SO₂NH(CH₂)₃N⁺(CH₃)₃]phenyl | H—P(=O)(O⁻)(OCH₃) |
| 525 | 2,5-diethyl-[SO₂NH(CH₂)₃N⁺(CH₃)₃]phenyl | CH₃—P(=O)(O⁻)(OCH₃) |
| 526 | 2,3-dichloro-[SO₂NH(CH₂)₃N⁺(CH₃)₃]phenyl | CH₃—P(=O)(O⁻)(OCH₃) |
| 527 | 2,3-dimethoxy-[SO₂NH(CH₂)₃N⁺(CH₃)₃]phenyl | CH₃—P(=O)(O⁻)(OCH₃) |
| 528 | phenyl-SO₂N(C₂H₅)(CH₂)₃N⁺(CH₃)₃ | C₂H₅—P(=O)(O⁻)(OCH₃) |
| 529 | phenyl-SO₂N(C₂H₅)(CH₂)₃N⁺(CH₃)₃ | H—P(=O)(O⁻)(OC₂H₅) |
| 530 | methylphenyl-SO₂NH(CH₂)₃N⁺(CH₃)₃ | CH₃—P(=O)(O⁻)(OCH₃) |
| 531 | phenyl-CONH(CH₂)₃N⁺(CH₃)₃ | CH₃—P(=O)(O⁻)(OCH₃) |
| 532 | phenyl-CONH(CH₂)₃N⁺(CH₃)₃ | CH₃—P(=O)(O⁻)(OCH₃) |
| 533 | phenyl-COOCH₂CH₂N⁺(CH₃)₃ | CH₃—P(=O)(O⁻)(OCH₃) |

TABLE 1-continued
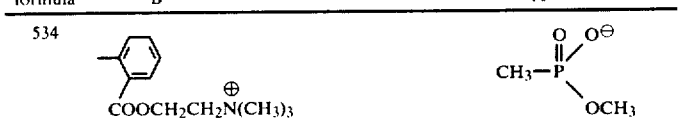
| formula | B | A |
|---|---|---|
| 534 | 2-CH₃-C₆H₄-COOCH₂CH₂N⁺(CH₃)₃ | CH₃-P(=O)(O⁻)(OCH₃) |
TABLE 2
[B—CH=CH—C₆H₄—C₆H₄—CH=CH—B']A  (600)
| formula | B | B' | A |
|---|---|---|---|
| 601 | 2-CH₃-C₆H₄-SO₂NH(CH₂)₃N⁺(CH₃)₃ | C₆H₅- | CH₃-P(=O)(O⁻)(OCH₃) |
| 602 | " | 2-Cl-C₆H₄- | H-P(=O)(O⁻)(OCH₃) |
| 603 | " | 2,3-(CH₃O)₂-C₆H₃- | CH₃-P(=O)(O⁻)(OCH₃) |
| 604 | " | 2,3-Cl₂-C₆H₃- | " |
| 605 | " | 3-COOCH₃-C₆H₄- | " |
| 606 | " | 4-SO₂CH₃-C₆H₄- | " |
| 607 | " | 3-F-C₆H₄- | " |
| 608 | " | 3-COOH-C₆H₄- | " |
| 609 | " | 3-CN-C₆H₄- | " |
| 610 | " | 4-CH(CH₃)₂-C₆H₄- | " |
| 611 | " | 2,4,5-(CH₃)₃-C₆H₂- | H-P(=O)(O⁻)(OCH₃) |

TABLE 2-continued $$\left[ B-CH=CH-\underset{}{\underset{}{\bigcirc}}-\underset{}{\underset{}{\bigcirc}}-CH=CH-B' \right] A \quad (600)$$

| formula | B | B' | A |
|---|---|---|---|
| 612 | 4-Cl, 3-CH₃, 5-SO₂NH(CH₂)₃N⊕(CH₃)₃ phenyl | phenyl | " |
| 613 | " | 2-Cl phenyl | CH₃—P(=O)(O⁻)(OCH₃) |
| 614 | " | phenyl | " |
| 615 | " | 3-OCH₃ phenyl | " |

The sulfonamides and carboxy amides used as starting materials of the compounds listed in Tables 1 and 2 can be prepared by methods which are known per se, for example as described in German Pat. No. 1,793,482, from the sodium salt of the corresponding sulfonic acid or carboxylic acid by conversion into the sulfonyl chloride or carboxylic acid chloride and condensation with the corresponding amine.

The carboxylates employed can likewise be obtained by methods which are known per se, for example as described in German Offenlegungsschrift 2,039,993.

TABLE 3

$$\left[ D \underset{}{\overset{N\diagdown N}{\diagup\diagdown}} \underset{}{\underset{}{\bigcirc}}-E \right] A \quad (700)$$

| formula | D | E | A |
|---|---|---|---|
| 701 | Cl—phenyl— | —SO₂NH(CH₂)₃N⊕(CH₃)₃ | CH₃—P(=O)(O⁻)(OCH₃) |
| 702 | Cl—phenyl— | —SO₂NH(CH₂)₃N⊕(CH₃)₃ | H—P(=O)(O⁻)(OCH₃) |
| 703 | Cl—phenyl— | —SO₂N(piperazinyl, N⊕(CH₂CH₂OH)(CH₃)) | CH₃—P(=O)(O⁻)(OCH₃) |
| 704 | Cl—phenyl— | —SO₂(CH₂)₂OCH(CH₃)—CH₂N⊕(CH₃)₃ | CH₃—P(=O)(O⁻)(OCH₃) |
| 705 | Cl—phenyl— | —SO₂(CH₂)₂OCH(CH₃)—CH₂N⊕(CH₃)₃ | H—P(=O)(O⁻)(OCH₃) |
| 706 | Cl—phenyl— | —SO₂(CH₂)₂OCH₂CH₂N⊕(CH₃)₃ | CH₃—P(=O)(O⁻)(OCH₃) |
| 707 | Cl—phenyl— | —SO₂(CH₂)₂OCH₂CH₂N⊕(CH₃)₃ | H—P(=O)(O⁻)(OCH₃) |

TABLE 3-continued (700)

[D–C(=N–N)–CH₂–C₆H₄–E]  A

| formula | D | E | A |
|---|---|---|---|
| 708 | 4-Cl-C₆H₄- | -SO₂(CH₂)₂O-CH₂CH₂N⁺(H)(CH₃)(cycloheptyl... ring) | CH₃-P(=O)(O⁻)-OCH₃ |
| 709 | 4-Cl-C₆H₄- | -SO₂(CH₂)₂OCH₂CH₂N⁺(C₂H₅)₂(CH₃) | CH₃-P(=O)(O⁻)-OCH₃ |
| 710 | 4-Cl-C₆H₄- | -SO₂(CH₂)₂OCH₂CH₂N⁺(C₄H₉)₂(CH₃) | CH₃-P(=O)(O⁻)-OCH₃ |
| 711 | 3,4-Cl₂-5-CH₃-C₆H₂- | -SO₂(CH₂)₂OCH(CH₃)-CH₂N⁺(CH₃)₃ | CH₃-P(=O)(O⁻)-OCH₃ |
| 712 | 3,4-Cl₂-5-CH₃-C₆H₂- | -SO₂(CH₂)₂OCH₂CH₂N⁺(CH₃)₃ | CH₃-P(=O)(O⁻)-OCH₃ |
| 713 | 3,4-Cl₂-5-CH₃-C₆H₂- | -SO₂CH₂-CH₂N⁺(CH₃)₃ | H-P(=O)(O⁻)-OCH₃ |
| 714 | 3,4-Cl₂-5-CH₃-C₆H₂- | -SO₂NH(CH₂)₃N⁺(CH₃)₃ | CH₃-P(=O)(O⁻)-OCH₃ |
| 715 | 3,4-Cl₂-5-CH₃-C₆H₂- | -COOCH₂CH₂N⁺(CH₃) | CH₃-P(=O)(O⁻)-OCH₃ |
| 716 | 3,4-Cl₂-5-CH₃-C₆H₂- | -SO₂NHCH₂CH₂N⁺(C₂H₅)₂(CH₃) | CH₃-P(=O)(O⁻)-OCH₃ |
| 717 | 4-Cl-C₆H₄- | -SO₂(CH₂)₂CONH(CH₂)₃N⁺(CH₃)₃ | CH₃-P(=O)(O⁻)-OCH₃ |
| 718 | 4-Cl-C₆H₄- | -SO₂(CH₂)₂CONH(CH₂)₃N⁺(CH₃)₃ | H-P(=O)(O⁻)-OCH₃ |
| 719 | 4-Cl-C₆H₄- | -SO₂(CH₂)₂CON(piperazinium-N,N-diCH₃) | CH₃-P(=O)(O⁻)-OCH₃ |
| 720 | 4-Cl-C₆H₄- | -SO₂(CH₂)₂CONH-CH₂-CH₂N⁺(CH₃)₃ | CH₃-P(=O)(O⁻)-OCH₃ |

TABLE 3-continued $$\left[D-\overset{N}{C}=\overset{N}{N}-\text{phenyl}-E\right] \quad A \quad (700)$$

| formula | D | E | A |
|---|---|---|---|
| 721 | Cl—C₆H₄— | —SO₂(CH₂)₂COOCH₂CH₂N⁺(CH₃)₃ | CH₃—P(=O)(O⁻)(OCH₃) |
| 722 | Cl—C₆H₄— | —SO₂(CH₂)₂COOCH(CH₃)—CH₂N⁺(CH₃)₃ | CH₃—P(=O)(O⁻)(OCH₃) |
| 723 | Cl—C₆H₄— | —SO₂(CH₂)₂COO(CH₂)₃N⁺(CH₃)₃ | CH₃—P(=O)(O⁻)(OCH₃) |
| 724 | Cl—C₆H₄— | —SO₂CH₂—CH(CH₃)—OCH₂CH₂N⁺(CH₃)(C₂H₅)₂ | CH₃—P(=O)(O⁻)(OCH₃) |
| 725 | Cl—C₆H₄— | —SO₂CH₂—CH(CH₃)—O(CH₂)₃N⁺(CH₃)₃ | CH₃—P(=O)(O⁻)(OCH₃) |
| 726 | Cl—C₆H₄— | —SO₂CH₂—CH(CH₃)—OCH₂CH₂N⁺(CH₃)(morpholino) | CH₃—P(=O)(O⁻)(OCH₃) |
| 727 | Cl—C₆H₄— | —SO₂CH₂—CH(CH₃)—OCH₂CH₂N⁺(CH₃)₃ | CH₃—P(=O)(O⁻)(OCH₃) |
| 728 | Cl—C₆H₄— | —SO₂CH₂—CH(CH₃)—OCH₂CH(CH₃)—N⁺(CH₃)₃ | H—P(=O)(O⁻)(OCH₃) |
| 729 | Cl—C₆H₄— | —SO₂CH₂—CH(CH₃)—O(CH₂)₃N⁺(piperidino)(CH₃) | H—P(=O)(O⁻)(OCH₃) |
| 730 | 3,5-di(CH₃,Cl)—C₆H₃— | —SO₂CH₂—CH(CH₃)—OCH₂CH₂N⁺(CH₃)₃ | CH₃—P(=O)(O⁻)(OCH₃) |
| 731 | Cl—C₆H₄— | —SO₂—N(piperazinyl-N⁺(CH₃)₂) | CH₃P(=O)(O⁻)(OCH₃) |

EXAMPLE 6

With stirring, 10.8 g of dimethyl methanephosphonate are added to a solution of 6.25 g of the compound of the formula

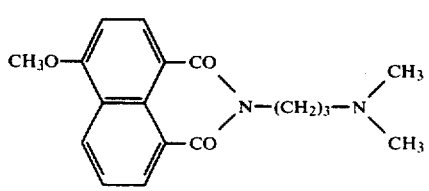

(800)

(m.p. 95° C.) in 30 ml of toluene. The mixture is heated for 2 hours at reflux temperature, whereupon the reaction product precipitates. After cooling to room temperature, the precipitate is collected by suction, washed with toluene and dried immediately, affording 5.6 g of the compound of the formula

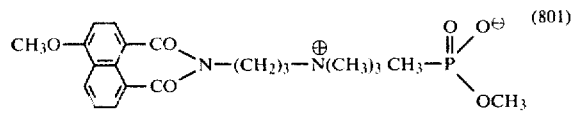

as a hygroscopic substance which deliquesces in air. The compound of the formula

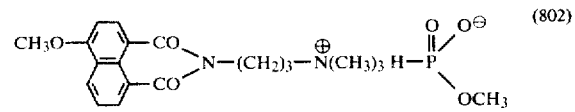

is obtained as a hygroscopic substance by repeating the above procedure, but using dimethyl phosphite instead of the phosphonate.

EXAMPLE 7

0.3 g of the fluorescent whitening agent of the formula (101), (201), (300) or (400) are dissolved in 270 ml of softened water. To this solution are added 0.3 g of the adduct of 1 mole of stearyl alcohol with 35 moles of ethylene oxide, 0.3 g of the adduct of 1 mole of p-tert-octylphenol with 8 to 9 moles of ethylene oxide and 30 ml of 95% ethanol. Then 8 g of a polyacrylic staple fabric (Courtelle ®) are put into this fluorescent whitener solution, which has been warmed to 50° C. The temperature is raised to 100° C. in the course of 10 minutes and kept thereat for 20 minutes. After cooling to 50° C. in the course of 5 minutes, the fabric is rinsed in softened water, centrifuged, and dried with an iron at 140°–150° C. The treated fabric has a strong white effect.

EXAMPLE 8

0.3 g of the fluorescent whitening agent of the formula (101), (201), (300) or (400) are dissolved in 270 ml of softened water. To this solution are added 0.3 g of the adduct of 1 mole of stearyl alcohol with 35 moles of ethylene oxide, 0.3 g of the adduct of 1 mole of p-tert-octylphenol with 8 to 9 moles of ethylene oxide, 30 ml of 95% ethanol and 0.67 g of sodium tripolyphosphate. Then 8 g of a polyacrylonitrile fabric are put into this fluorescent whitener solution, which has been warmed to 30° C. The temperature is raised to 60° C. in the course of 10 minutes and kept thereat for 20 minutes. The fabric is rinsed in softened water, centrifuged, and dried with an iron at 160°–170° C. The treated fabric has a strong white effect.

EXAMPLE 9

0.3 g of the fluorescent whitening agent of the formula (101), (201), (300) or (400) are dissolved in 270 ml of softened water. To this solution are added 0.3 g of the adduct of 1 mole of stearyl alcohol with 35 moles of ethylene oxide, 0.3 g of the adduct of 1 mole of p-tert-octylphenol with 8 to 9 moles of ethylene oxide, 30 ml of 95% ethanol and 0.16 g of sodium phosphate. Then 8 g of a polyamide fabric are put into this fluorescent whitener solution, which has been warmed to 50° C. The temperature is raised to 100° C. in the course of 10 minutes and kept thereat for 20 minutes. After cooling to 50° C. in the course of 5 minutes, the fabric is rinsed in softened water, centrifuged, and dried with an iron at 180° C. The treated fabric has a strong white effect.

EXAMPLE 10

0.3 g of the fluorescent whitening agent of the formula (101), (201), (300) or (400) are dissolved in 270 ml of softened water. To this solution are added 0.3 g of the adduct of 1 mole of stearyl alcohol with 35 moles of ethylene oxide, 0.3 g of the adduct of 1 mole of p-tert-octylphenol with 8 to 9 moles of ethylene oxide and 30 ml of 95% ethanol. A piece of cotton (8 g) is padded with this fluorescent whitener solution to a pick-up of 75% at 20°–25° C. The fabric is then put into a dyeing machine which contains sufficient warm water of 30° C. to give a liquor ratio of 1:25. The temperature is then raised to 60° C. in the course of 10 minutes and kept thereat for 20 minutes. The cotton fabric is then rinsed with softened water, centrifuged, and dried at 70° C. The treated fabric has a strong white effect.

EXAMPLE 11

A non-whitened cotton fabric is put at 20°–25° C. in a liquor ratio of 1:20 into a bath which contains, per liter, 5 g of a plasticiser preparation consisting of 3.9% of an alkyl trimethylammonium chloride (e.g. commercially available Arquad 2HT 75 ®) and 0.1% of a fluorescent whitening agent of the formula (101) or (300). The fabric is treated with the bath for 10 minutes, then rinsed and dried at 80° C. The treated fabric has a strong white effect.

EXAMPLE 12

Freshly spun, stretched polyacrylonitrile wet cable (corresponding to 3 g dry weight) is immersed, while still moist, at 45° C. for 4 seconds in 100 ml of an aqueous liquor which contains 0.0005% of the fluorescent whitening agent of the formula (101), (201), (300) or (400), and which has been adjusted with concentrated oxalic acid solution to pH 4. The wet cable is subsequently rinsed briefly with water and dried at 90° to 100° C. The treated polyacrylonitrile cable has a good white effect.

The whitening can also be carried out for example at pH 6 (adjusted by addition of sodium acetate). Raising the temperature of the liquor, for example to 40° C., increases the rate of exhaustion.

Stronger white effects are obtained by increasing the concentration of fluorescent whitening agent e.g. to 0.005%.

EXAMPLE 13

A rinsed, stretched, and undried polyacrylonitrile cable obtained by the sodium thiocyanate wet spinning process is immersed at 45° C. in the liquor ratio 1:100 for 4 seconds in an aqueous solution which contains, per liter, 0.1 g of the fluorescent whitening agent of the formula (101), (201), (300) or (400), and 0.5 ml of 85% formic acid (pH value of the solution: 4).

The cable is subsequently briefly rinsed in water and dried at 95° C. in the air. The polyacrylonitrile cable has a strong white effect.

What is claimed is:

1. A cationic fluorescent whitening agent of the formula

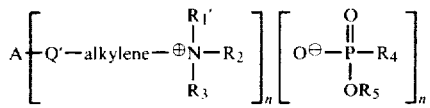

wherein
- A is a radical selected from the group consisting of 1,3-diarylpyrazolines, 4,4'-distyrylbiphenyls or naphthalimides,
- Q' is —SO$_2$—alkyleneoxy containing 2 to 4 carbon atoms, —SO$_2$— alkylene—COO—containing 2 to 4 carbon atoms, —SO$_2$, —COO—, —SO$_2$—alkylene —CON(R$_6$)—containing 2 to 4 carbon atoms in the alkylene moiety, —SO$_2$N(R$_6$)— or —CON(R$_6$)—, wherein R$_6$ is hydrogen, unsubstituted or substituted alkyl of 1 to 5 carbon atoms substituted by cyano, carbamoyl, carboxyl, carbalkoxy, hydroxyl, halogen or alkoxy of 1 to 4 carbon atoms, or together with R$_1$' forms a piperazine radical,
- bridging member alkylene is a bivalent straight or branched alkylene of 2 to 20 carbon atoms,
- R$_1$' is unsubstituted or substituted alkyl of 1 to 6 carbon atoms substituted by halogen, cyano, hydroxyl, alkoxycarbonyl of 1 to 4 carbon atoms or alkylcarbonyloxy of 1 to 4 carbon atoms, alkenyl of 2 to 4 carbon atoms, aralkyl or aralkyl substituted on the benzene ring by halogen, alkyl of 1 to 4 carbon atoms or alkoxy of 1 to 4 carbon atoms, or together with R$_6$ forms a piperazine radical or together with R$_2$ forms a heterocyclic ring selected from the group consisting of piperidine, pyrrolidine or morpholine, or said heterocycles substituted by alkyl groups of 1 to 4 carbon atoms,
- R$_2$ is unsubstituted or substituted alkyl of 1 to 6 carbon atoms substituted by halogen, cyano, hydroxyl, alkoxycarbonyl of 1 to 4 carbon atoms or alkylcarbonyloxy of 1 to 4 carbon atoms, alkenyl of 2 to 4 carbon atoms, aralkyl or aralkyl substituted on the benzene ring by halogen, alkyl of 1 to 4 carbon atoms or alkoxy of 1 to 4 carbon atoms, or together with R$_1$' forms a heterocyclic ring selected from the group consisting of piperidine, pyrrolidine or morpholine or said hetercycles substituted by alkyl group of 1 to 4 carbon atoms,
- R$_3$ is alkyl of 1 to 4 carbon atoms,
- R$_4$ is hydrogen, unsustituted or substituted alkyl of 1 to 4 carbon atoms substituted by hydroxyl, cyano, alkylcarbonyloxy or alkoxycarbonyl each containing 1 to 4 carbon atoms in the alkyl moiety,
- R$_5$ is alkyl of 1 to 4 carbon atoms, and
- n is 1 or 2.

2. A cationic fluorescent whitening agent according to claim 1 of the formula

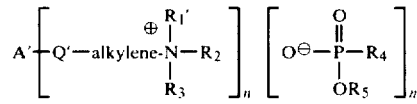

wherein Q', R$_1$', R$_2$ to R$_5$ and n are as defined in claim 1 and A' is a radical of the formula

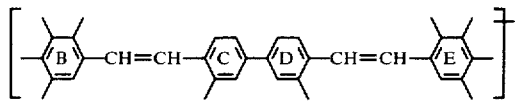

or of the formula

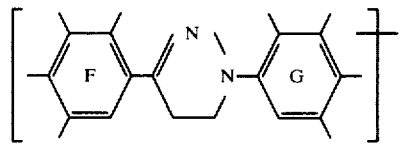

the benzene rings of which formulae can also be substituted at the indicated positions by non-chromophoric substituents.

3. A cationic fluorescent whitening agent according to claim 2 of the formula

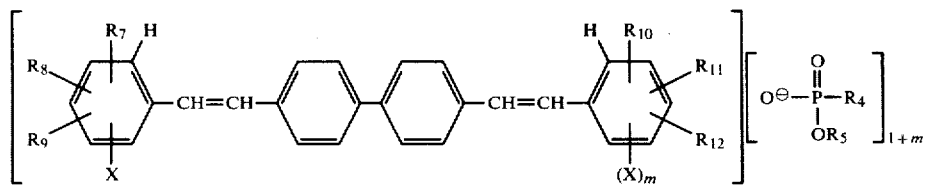

wherein R$_4$ and R$_5$ are as defined in claim 3 and m is 0 or 1, R$_7$ is hydrogen, alkyl of 1 to 4 carbon atoms, alkoxy of 1 to 4 carbon atoms or halogen, R$_8$ is hydrogen, alkyl of 1 to 4 carbon atoms, alkoxy of 1 to 4 carbon atoms or halogen, R$_9$ is hydrogen or alkyl of 1 to 4 carbon atoms, R$_{10}$, R$_{11}$ and R$_{12}$, if m is 1, have the meanings of R$_7$, R$_8$ and R$_9$ or, if m is 0, each of R$_{10}$, R$_{11}$ and R$_{12}$ independently is hydrogen, alkyl of 1 to 4 carbon atoms, alkoxy of 1 to 4 carbon atoms or halogen, and X is the radical

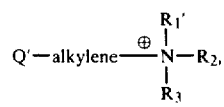

wherein Q', R$_1$', R$_2$ and R$_3$ are as defined in claim 3.

4. A cationic fluorescent whitening agent according to claim 3 of the formula

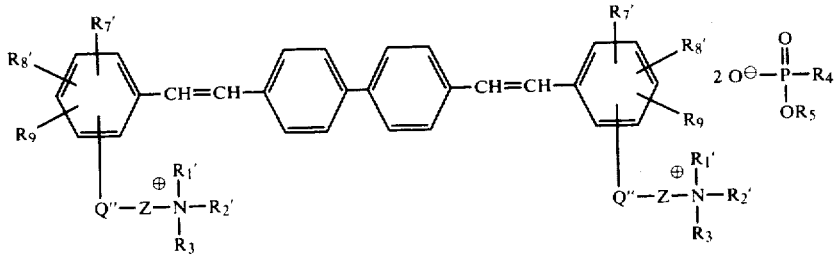

wherein
Q" is —COO—, —CON(R₆)— or —SO₂N(R₆)—,
R₁' is unsubstituted or substituted alkyl, alkenyl or aralkyl, together with R₆ is a piperazine radical or together with R₂' is a pyrrolidine, piperidine or morpholine radical,
R₂' is unsubstituted or substituted alkyl, alkenyl or aralkyl or together with R₁' is a pyrrolidine, piperidine or morpholine radical,
R₃ is alkyl of 1 to 4 carbon atoms,
R₄ is hydrogen or unsubstituted or substituted alkyl,
R₅ is alkyl of 1 to 4 carbon atoms,
R₆ is hydrogen, unsubstituted or substituted alkyl of 1 to 5 carbon atoms or together with R₁' is a piperazine radical,
R₇' is hydrogen, chlorine, alkyl of 1 to 4 carbon atoms or alkoxy of 1 to 4 carbon atoms,
R₈' is hydrogen, chlorine, alkyl of 1 to 4 carbon atoms or alkoxy of 1 to 4 carbon atoms,
R₉ is hydrogen or alkyl of 1 to 4 carbon atoms, and
Z is alkylene of 2 to 5 carbon atoms.

R₂' is unsubstituted or substituted alkyl, alkenyl or aralkyl or together with R₁' is a pyrrolidine, piperidine or morpholine radical,
R₃ is alkyl of 1 to 4 carbon atoms,
R₄ is hydrogen or unsubstituted or substituted alkyl,
R₅ is alkyl of 1 to 4 carbon atoms,
R₁₃, R₁₄ and R₁₅ each independently of the other, is hydrogen, chlorine, alkyl of 1 to 4 carbon atoms or alkoxy of 1 to 4 carbon atoms,
Y is alkylene of 2 or 3 carbon atoms, —N(R₆)— alkylene containing 2 to 5 carbon atoms in the alkylene moiety, alkyleneoxyalkylene containing altogether 4 to 8 carbon atoms, alkylene—COO—alkylene or alkylene—CON(R₆)—alkylene, each containing altogether 4 to 8 carbon atoms in the alkylene moiety, and
R₆ is hydrogen, unsubstituted or substituted alkyl of 1 to 5 carbon atoms or together with R₁' is a piperazine radical.

6. A cationic fluorescent whitening agent according to claim 4 of the formula

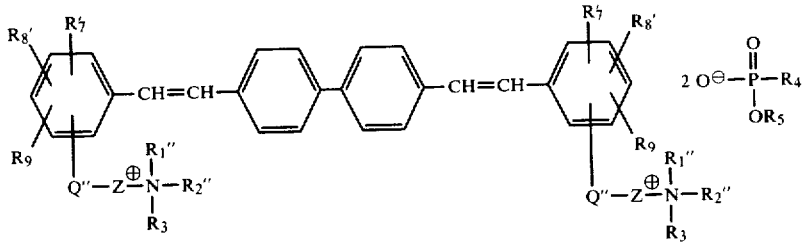

5. A cationic fluorescent whitening agent according to claim 2 of the formula

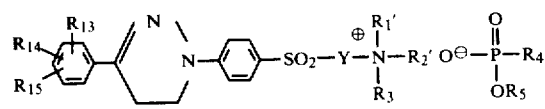

wherein
R₁' is unsubstituted or substituted alkyl, alkenyl or aralkyl, together with R₆ is a piperazine ring or together with R₂' is a pyrrolidine, piperidine or morpholine radical, wherein R₃ to R₅, R₇', R₈', R₉ and Z are as defined in claim 5,
Q" is —COO—, —CON(R₆)— or —SO₂N(R₆)—, wherein R₆ is hydrogen, unsubstituted or substituted alkyl of 1 to 5 carbon atoms or together with R₁" is a piperazine radical,
R₁" is unsubstituted alkyl of 1 to 4 carbon atoms or together with R₆ is a piperazine radical, and
R₂" is unsubstituted alkyl of 1 to 4 carbon atoms.

7. A cationic fluorescent whitening agent according to claim 5 of the formula

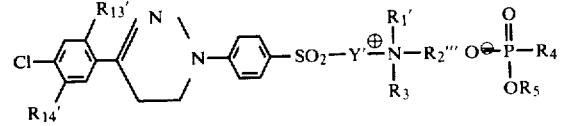

wherein
R₃, R₄ and R₅ are as defined in claim 6,
R₁'" is unsubstituted or substituted alkyl of 1 to 4 carbon atoms, together with R₆ is a piperazine radical or together with $R_2'''$ is a pyrrolidine, piperidine or morpholine radical, $R_2'''$ is unsubstituted or substituted alkyl of 1 to 4 carbon atoms or together with $R_1'''$ is a pyrrolidine, piperidine or morpholine radical, $R_{13}'$ represents hydrogen or alkyl of 1 to 4 carbon atoms, $R_{14}'$ represents hydrogen or chlorine, Y' represents alkylene of 2 or 3 carbon atoms, —N(R$_6$)— alkylene containing 2 to 5 carbon atoms in the alkylene moiety, alkyleneoxyalkylene or alkylene—COO— alkylene, each containing altogether 4 to 6 carbon atoms in the alkylene moiety, or alkylene—CON(R$_6$)— alkylene containing altogether 4 to 8 carbon atoms in each alkylene moiety, and $R_6$ represents hydrogen, unsubstituted or substituted alkyl of 1 to 5 carbon atoms or together with $R_1'''$ represents a piperazine radical.

8. A cationic fluorescent whitening agent according to claim 6 of the formula

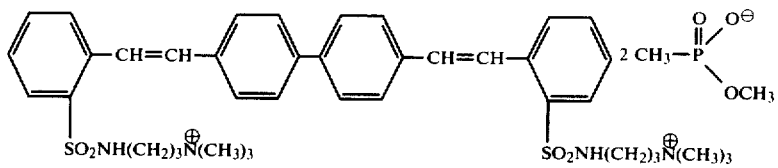

9. A cationic fluorescent whitening agent according to claim 6 of the formula

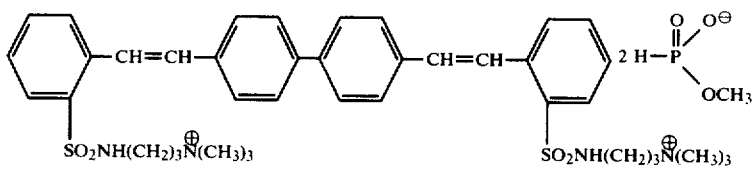

* * * * *